United States Patent [19]

Meinecke et al.

[11] 4,442,836

[45] Apr. 17, 1984

[54] BLOOD LANCET DEVICE

[75] Inventors: Dieter Meinecke; Werner Schmidt, both of Mannheim; Rudolf Schüssler, Lampertheim; Rainer van Rijckevorsel, Brühl, all of Fed. Rep. of Germany

[73] Assignee: Clinicon Mannheim GmbH, Mannheim, Fed. Rep. of Germany

[21] Appl. No.: 245,010

[22] Filed: Mar. 18, 1981

[30] Foreign Application Priority Data

Mar. 22, 1980 [EP] European Pat. Off. ............ 3011211
Nov. 15, 1980 [DE] Fed. Rep. of Germany ..... 80107078

[51] Int. Cl.³ ............................................. A61B 17/34
[52] U.S. Cl. ................................. 128/314; 128/329 R; 604/137; 604/157
[58] Field of Search ............... 128/329 R, 314, 315, 128/329 A, 330, 638; 604/156, 157, 136, 137, 46, 47

[56] References Cited

U.S. PATENT DOCUMENTS

| | | | |
|---|---|---|---|
| 236,084 | 12/1880 | Reinhold et al. | 128/314 |
| 2,531,267 | 11/1950 | Harnisch | 604/136 |
| 3,030,959 | 4/1962 | Grunert | 128/329 |
| 4,120,303 | 10/1978 | Villa-Massone et al. | 128/330 |
| 4,230,118 | 10/1980 | Holman et al. | 128/329 R X |

*Primary Examiner*—Michael H. Thaler
*Attorney, Agent, or Firm*—Sprung, Horn, Kramer & Woods

[57] ABSTRACT

A blood lancet device for taking blood for diagnostic purposes, having a housing with an exit opening for the lancet, a lancet guide for guiding the puncturing and return movement of the lancet, a spring drive for movement of the lancet and a stop by means of which the lancet is held in a position remote from the part of the body from which blood is to be taken. In the region of the exit opening for the lancet, a release element is present in the housing, the release element being in operative connection with the stop.

13 Claims, 8 Drawing Figures

FIG. 4a.
FIG. 4b.
FIG. 5.
FIG. 6.
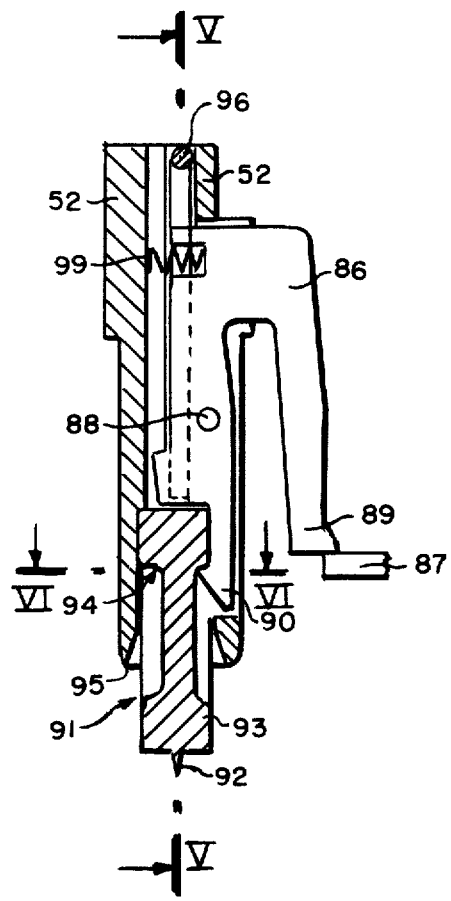
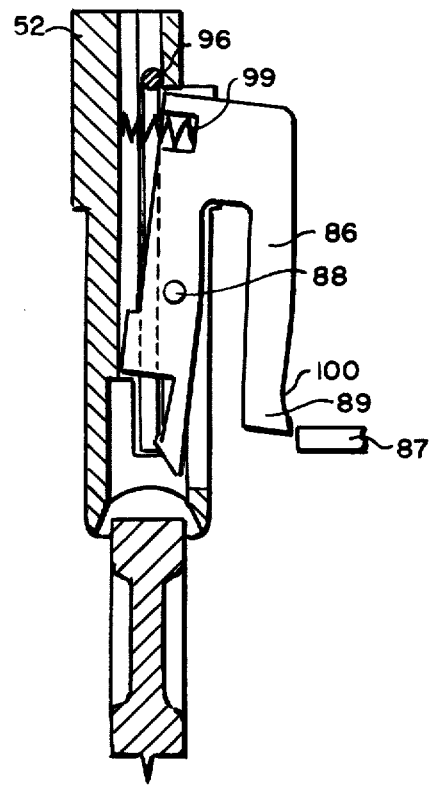
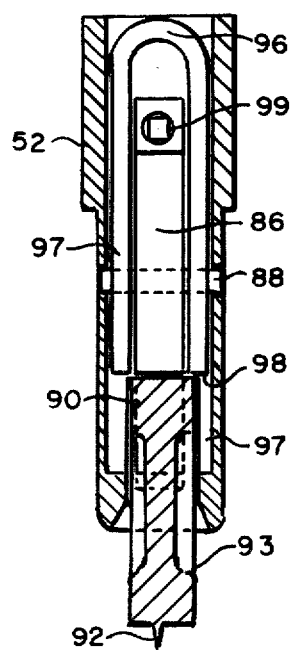
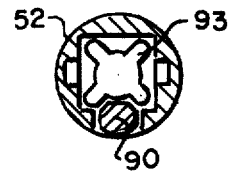

BLOOD LANCET DEVICE

BACKGROUND OF THE INVENTION

The present invention is concerned with a blood lancet device for taking blood for diagnostic purposes, this device having a housing with an exit opening for the lancet, a lancet guide for guiding the puncturing and return movement of the lancet, a spring drive for movement of the lancet and a stop by means of which the lancet is kept in a position remote from the part of the body from which blood is to be taken.

In order to obtain small amounts of blood for diagnostic purposes, lancets are used which a laboratory assistant briefly sticks into a patient's finger tip or into some other suitable part of the patient's body. A disadvantage of this is that the patient can see what is happening and the nature of the resulting wound depends upon the user of the lancet and cannot, therefore, be reproduced. Furthermore, it is quite common that a second person must carry out the puncturing operation since the degree of protection against self-injury is very great.

Blood lancet devices are also known, with the help of which a patient can sample his own blood. However, here again, the puncturing operation is generally visible. Furthermore, in the case of these devices, there is a possibility that a lancet intended for single use is employed several times successively by operating the cocking lever of the device. This results in a considerable danger of infection.

One example of such a known device is described in German Patent Specification No. 459,483. In this case, the lancet is driven for the puncturing movement by means of a spiral spring which can be tensioned by operating a pull rod connected to the lancet. In the tensioned state, a stop connected with the lancet engages in a recess provided laterally in the collar-shaped housing of the lancet device. A patient who wishes to use this known device for sampling his own blood must overcome a considerable feeling of inhibition in order to activate the lateral release knob without simultaneously automatically pulling away the finger tip or other part of the body from which the blood is to be taken. A further disadvantage of this known device is that the driving spring can oscillate, which can result in a jagged puncturing and, consequently, in wounds which heal with difficulty.

SUMMARY OF THE INVENTION

It is an object of the present invention to provide an improved blood lancet device of the above-described type which is better to use than the previously known devices for the self-sampling of blood. The self-sampling of blood is of great importance, especially for self-monitoring by diabetics, because this not only leads to an unburdening of medical personnel but also makes possible a substantially better adjustment of the medical treatment of diabetics. In this way, in particular, the danger of subsequent damage due to diabetes can be reduced or avoided.

Thus, according to the present invention, there is provided a blood lancet device for taking blood for diagnostic purposes, the device having a housing with an exit opening for the lancet, a lancet guide for guiding the puncturing and return movement of the lancet, a spring drive for movement of the lancet and a stop by means of which the lancet is held in a position remote from the part of the body from which blood is to be taken, wherein, in the region of the exit opening for the lancet, a release element is present in the housing, the release element being in operative connection with the stop.

By means of the device according to the present invention, the puncturing movement of the lancet device is released by pressing it on to the part of the body from which blood is to be taken. This has the substantial advantage that the user of the blood lancet device can no longer pull back during the releasing of the lancet. This also ensures a uniform pressing of the device on, for example, a finger tip. This is of great importance for reproducibly achieving a wound which is as optimal as possible. In contradistinction thereto, in the case of the previously known lancet devices, it could easily happen that, due to a convulsively firm pressing of the device on a finger tip, too deep a wound was obtained, which healed with difficulty, or that the wound, due to sudden withdrawal of the device, was too small so that insufficient blood could be obtained.

According to a preferred embodiment of the device according to the present invention, the release element is constructed as a release key set into the housing so that it is not visible to the user at the moment of puncturing. This also reduces the degree of inhibition and a more uniform wound is obtained.

The spring drive for the lancet preferably comprises two different springs. One of these two springs performs the puncturing operation and is so constructed that, in its field of use, it has a stronger force than the second spring, which brings about the return movement of the lancet. In this way, the puncturing and return movement are separated from one another and their particular speed and force can be adapted to use requirements. The stronger spring preferably acts against the weaker one in the course of the puncturing operation. An appropriate mechanism, which is described hereinafter by way of example, interrupts the action of the stronger spring at a definite point of the lancet stroke. The lancet then only moves a further short distance due to its inertia and the force of the spring bringing about the puncturing operation and, subsequently, is moved back in the direction of the initial position by means of the spring bringing about the return movement.

The previously described disconnection of the spring bringing about the puncturing movement from the lancet can, according to a further preferred embodiment of the present invention, be achieved with the help of an angle lever which is driven by this spring. Such an angle lever also makes possible a compact and economical construction of the device.

For the production of the positive connection between the release element and the stop of the lancet, according to a further preferred embodiment of the present invention, use is made of a pusher which is connected to the release element, the release element being simultaneously pushed back by a pressure spring, after release, into its starting position. This pusher connection has few mechanical constructional elements and is, therefore, simple to make and dependable in operation. However, numerous other ways of achieving the positive connection between the release and the stop are conceivable, for example, lever connections, cables or also hydraulic devices.

The lancet device is preferably provided with a lancet holder in which the lancet is exchangeably mounted but with the strength necessary for the puncturing operation. In this way, a new lancet can be used for each puncturing operation so that cleaning and sterilizing of the lancet tip are unnecessary. In order to make the changing of the lancet as simple as possible, according to a further preferred embodiment of the present invention, the lancet holder can be moved, via an operating lever, in the direction of the exit opening of the lancet for the reception of the lancet. As the operating lever, there can advantageously be used the same device which also serves for tensioning the lancet device.

Further preferred embodiments, serve, in toto, the purpose of making the changing of the lancet one operation which, without the user having to do anything, automatically takes place between each usage of the lancet device. For this purpose, there is provided an automatic ejector with a repetition stop which is preferably made in the form of a ratchet lever connected with the holding device for the lancet in the lancet holder. This ratchet lever has, on the one hand, a ratchet which acts positively with a corresponding part of the lancet. On the other hand, the ratchet lever cooperates with an abutment which is in a fixed position in the housing of the lancet device. If the loading device for the lancet is, for the reception of a new lancet, moved by the user via an appropriate lever device or operating button in the direction of the lancet exit opening, then the end of the ratchet lever remote from the ratchet impinges against the abutment and the lancet is automatically ejected. In order to simplify this ejection procedure, a movable weight may be provided in the lancet holder which lies against the lancet inserted into the holding device. Due to the inertia of this weight, the ejection of the lancet at the moment at which the ratchet lever impinges against the abutment is made easier.

After ejection of the used lancet, the ratchet lever is, according to a further preferred embodiment of the present invention, brought by an appropriate spring into a position such that its operating arm no longer lies in the range of operation of the abutment when the lancet holder is moved in the direction of the exit opening of the device in order to receive a new lancet. The introduction of a new lancet presses back the ratchet lever against the force of the mentioned spring into a position in which its operating arm lies in the range of operation of the abutment. According to yet a further preferred embodiment of the present invention, the point of impingement of the abutment on the operating arm, the mounting axis of the ratchet lever and the ratchet are so arranged relative to one another that, upon movement of the lancet holder in the return direction, the abutment exerts a force on the ratchet lever in the closure direction of the ratchet. The ratchet lever and/or the abutment are made or mounted slightly elastically in order to make possible the return of the lancet holder with the inserted lancet. The ratchet lever preferably has a U-shape.

The result of the combination of the last-mentioned measures is that the lancet is automatically ejected after use and subsequently a new lancet can be inserted in a simple manner. Consequently, a repeated use of a lancet, with the considerable danger of infection resulting therefrom, is dependably avoided.

The present invention will now be described in more detail, with reference to the accompanying drawings, wherein:

BRIEF DESCRIPTION OF THE DRAWINGS

FIG. 4a shows a preferred embodiment of a lancet holder for use in a lancet device according to the present invention in side view and partially in section, with the lancet inserted;

FIG. 4b shows a side view partially in section of the lancet holder according to FIG. 4a after ejection of the lancet;

FIG. 5 shows a section through the lancet holder according to FIG. 4a along the line V—V; and FIG. 6 shows a section through the lancet holder according to FIG. 4a along the line VI—VI.

DETAILED DESCRIPTION OF THE INVENTION

Figure 1A:
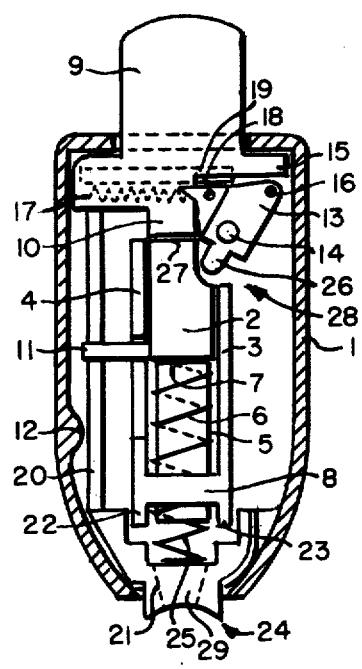
FIG. 1a shows a side view of a blood lancet device according to the present invention in a non-tensioned state with the housing cover removed.
Figure 1B:
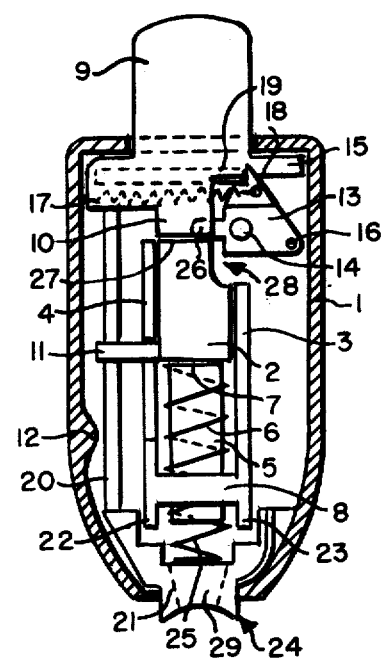
FIG. 1b shows a side view of the blood lancet device according to FIG. 1a in a tensioned and stopped state.

The blood lancet device illustrated in FIGS. 1a and 1b consists essentially of a housing 1 and a lancet holder 2 arranged therein. The lancet holder 2 is laterally held by sliding surfaces 3 and 4. The upper and lower side of the lancet holder 2 is guided by the walls of the housing. It is to be understood that numerous other guide means can also be used for guiding the lancet holder. A clamp holder is provided for the reception of the lancet in the lancet holder 2. The projecting lower end 5 of the lancet holder is cylindrically shaped and is encompassed by a pressure spring 6 which lies against a stop 7 of the lancet holder 2 and against a bridge 8 which is fixed on to the housing 1. For the reception of the lancet, the lancet holder 2 is moved downwardly and the lancet is inserted into the opening with the clamp holder lying in the axis of the lancet holder. In order to be able to move the lancet holder downwardly against the elastic force of the spring 6, an operating knob 9 is provided which projects from the housing 1 and is connected via a flange 10 with the lancet holder 2. A lever 11 is connected with the clamp holder in the lancet holder 2 which lever 11, during downward movement of the lancet holder 2, impinges against a cam 12 projecting from the wall of the housing and is thereby subjected to a tilting movement. During this tilting movement, the lancet clamp holder is freed and the lancet itself can fall out of the blood lancet due to its own weight. Thereafter a new lancet can be inserted, which is securely received in the clamp holder. The lever 11 itself is subject to spring force and is forced back into its initial position by the spring.

For the automatic operation of the blood lancet for the puncturing operation, an angle lever 13 is provided which can be tilted about an axis 14. Upon pressing down the knob 9, a projection 15 of the knob 9 engages on a pin 16 of the angle lever 13 and rotates the angle lever 13 clockwise against the force of a spring 17. One end of the spring 17 is fixed to the housing and the other end to an arm 18 of the angle lever 13. When the knob 9 is completely pressed down, an arm 18 snaps behind the end of the cross-piece 19 (indicated by a broken line) and stops there. The cross-piece 19 is directly connected via a rod 20 with a releaser 21. The releaser 21 is guided by the pillars 22 and 23 of the bridge 8. It is arranged to be movable in the same direction as the lancet holder 2 in an opening 24 of the housing 1. The releaser contains an exit opening 29 (indicated by broken lines) for the lancet. The releaser 21 is slightly forced out of the opening by a spring 25. The indicated position shows the releaser 21 in the non-tensioned, i.e. the non-operated, state in which it projects slightly out of the housing 1.

When the arm 18 is stopped via the cross-piece 19, a striker 26 of the angle lever 13 is situated above a surface 27 of the lancet holder 2. This position is illustrated in FIG. 1b.

By pressing the blood lancet device against the point at which blood is to be taken, the releaser 21 is pressed into the housing 1, the rod 20 and the cross-piece 19 thus moving upwardly. The arm 18 of the angle lever 13 is freed and, under the force of the pulling spring 17, the angle lever 13 is rotated about its axis. By means of the striker 26, the angle lever 13 presses the lancet holder 2 downwardly with a sudden movement, puncturing by the lancet taking place at the end of this movement. After puncturing has taken place, the striker 26 slips into a recess 28 on the lancet holder 2 and thereby frees the lancet holder for a backward movement into its resting position, this backward movement being brought about by the spring 6. The stroke path of the puncturing movement is so determined by the means described hereinafter that it causes an optimum puncturing wound. In any case, it is so small that the lever 11 and the cam 12 do not touch.

After this operation, the knob 9 is actuated and the housing 1 with the opening 24 pointing downwardly held over a collecting dish or the like. When the lever 11 reaches the cam 12, the clamp holder is opened and the lancet can fall out freely. The puncturing operation and the removal of the lancet are thus ended. It is to be observed that, during this procedure, the lancet no longer needs to be touched by the hand. Simultaneously the device is tensioned by the same operation.

Figure 2:
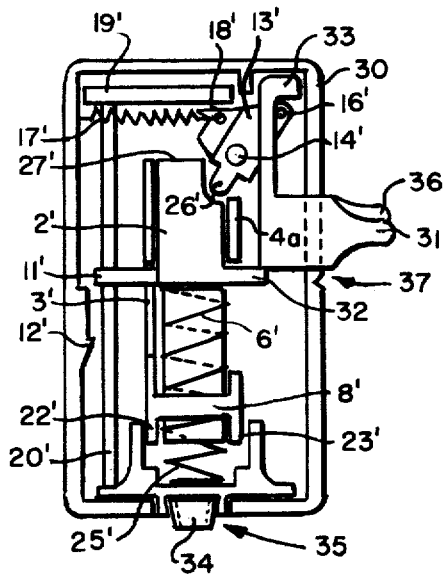
FIG. 2 shows another embodiment of the blood lancet device again from the side and with the housing cover removed.

In the automatic blood lancet shown in FIG. 2, the principal constructional features of the blood lancet of FIG. 1 are retained. However, changes are made in the shape of the housing, of the pressure knob and of the releaser. In the case of this blood lancet, the lancet holder 2' is moved downwardly in a housing 30, via an adjustment lever 31, for the reception of a lancet. The adjustment lever 31 engages a projection 32 of the lancet holder 2'. By means of a cam 33 on the adjustment level 31, during the downward movement of the adjustment lever 31, the pin 16' of the angle lever 13' and thus the angle lever 13' itself is taken along and rotated about the axis 14'. The arm 18' comes to lie behind the end of the cross-piece 19' and is thereby stopped. The striker 26' of the angle lever then lies against the surface 27' of the lancet holder 2'. The lancet holder 2' is guided by sliding surfaces 3' and 4a. The pressure spring 6' presses the lancet holder 2' into its indicated resting position. The rods 22' and 23' of the bridge 8' serve as sliding surfaces for a releaser 34 which projects out of an opening 35 of the housing 30. The pressure spring 25' presses the releaser 34 downwardly. The releaser 34 is connected with the cross-piece 19' via rod 20'.

In addition to the adjustment lever 31, a stop piece 36 is provided which, upon pressing down the adjustment lever 31, can be engaged into a notch 37. In this way, the lancet holder 2' is fixed in its lower position, the insertion of the lancet itself thereby being simplified. The clamp holder for the lancet has the opening lever 11' with impingement cam 12' as described in FIGS. 1a and 1b.

By means of an appropriate adjustment between the surface 27' and the size of the striker 26', the stroke length of the lancet holder 2' can be adjusted very precisely. In practical experiments, it has been found that, by appropriate adjustment of the springs 6' and 17', a very precise reproducibility of the depth of puncturing can be achieved. The puncturing operation takes place very quickly so that it can scarcely be analyzed in detail. In any case, by means of the relative length of the striker 26' and of the surface 27' and their particular extent, the stroke position of the lancet holder 2' is fixed in which engagement between the angle lever 13' and the holder 2' is interrupted. At this moment, the spring 17' no longer acts in the puncturing direction. However, because of its inertia, the holder 2' still moves downwardly a definite and, as the above-mentioned practical experiments have shown, precisely reproducible path length against the force of the spring 6'. After the reversal point, the holder 2, 2' is returned by the spring 6, 6' into its starting position, which is illustrated in FIGS. 1a and 2.

By means of these measures, the magnitude of the puncture wound can be predetermined. In the case of every operation of the blood lancet, the puncture wounds remain the same. The cam 12', in combination with the lever 11', represents an ejection mechanism which, in the case of each loading procedure, allows the lancet to fall out of the clamp holder.

Figure 3:
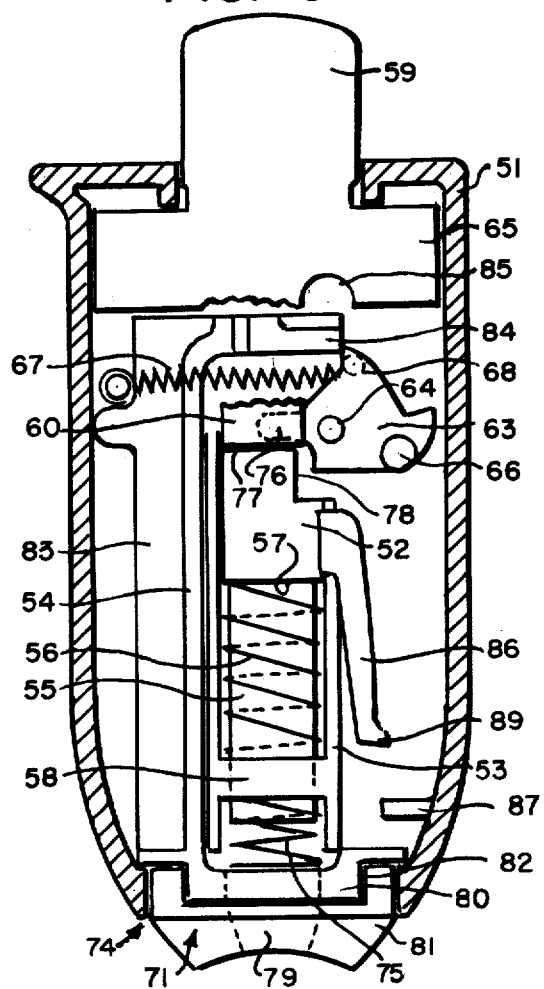
FIG. 3 shows a third embodiment of a blood lancet device according to the present invention in a tensioned and stopped state and in the same view as in the case of the above FIGS., but with partly cut-away parts.

FIG. 3 shows a further embodiment of the present invention in which the constructional parts corresponding to those in the previously described embodiments are indicated with reference numerals which are obtained by adding the figure 50 to the reference numerals employed in FIG. 1 for the corresponding parts.

The embodiment of FIG. 3 comprises a housing 51, a lancet holder 52, sliding surfaces 53 and 54, a projecting end 55 of a lancet holder 52, a pressure spring 56 for the return of holder 52 and which abuts against a stop 57, a bridge 58, an operating knob 59 with a flange 60, and an angle lever 63, which can be tiltable a out an axis 64 and is tilted by a projection 65 of the operating knob 50 acting on a pin 66. Reference numeral 67 indicates a spring by means of which, via the angle lever 63, the puncturing operation is carried out.

There are some differences from the previously described Figures in the construction of the constructional elements for the release of the puncturing operation. The releaser indicated in its totality by reference numeral 71, which lies in the housing opening 74, consists, in the case of the illustrated embodiment, of two parts, namely, a releaser base 80 and a releaser attachment 81 which, via an appropriate clamp holder 82, can be exchangeably connected with the releaser attachment. Both parts are penetrated by the lancet exit opening 79 (indicated by broken lines) and are together loaded by spring 75 in the direction of the exit opening. Various releaser attachments can be provided for the device, which differ slightly in their thickness. Since the stroke length of the lancet holder and thus of the lancet relative to the housing is, as previously described, reproducible, the depth of penetration into the part of the body pressed against the releaser attachment 81 becomes deeper, as this releaser attachment becomes less thick. By means of this simple measure, the depth of penetration into the skin of the individual patient can be determined in a very advantageous manner and thus can also be optimized in that a sufficiently productive and, at the same time, rapidly healing wound results.

Furthermore, the embodiment according to FIG. 3 differs in that the connecting rod 20 and the cross-piece 19 are replaced by a one-piece pusher 83 which transmits the release movement from the releaser 71 to the angle lever 63. This is illustrated in FIG. 3 in the tensioned and stopped position (corresponding to FIG. 1b), in which the end 84 of the pusher 83 is in engagement with the arm 68 of the angle lever 63 in order to stop it. If, upon pressing the releaser 71 on to an appropriate part of the body from which blood is to be taken, the pusher 83 moves upwardly, then the angle lever 63 is freed and the striker 76 impinges upon the upper surface 77 of the lancet holder 52 and guides this downwardly in the puncturing operation. As hereinbefore described, the puncturing operation is ended when the striker 76 enters into the recess 78 of the lancet holder and thus the positive connection is interrupted. Thereafter, the return movement commences, which is brought about by the spring 56. The operating knob 59 has, in the case of the illustrated embodiment, a recess 85 in order that, upon tensioning the device, it does not come into contact with the axis 64. The flange 60 of the operating knob 59 is, in FIG. 3, illustrated cut off in order that the spring 67 and the upper part of the pusher 83 can better be seen.

A further special feature of the embodiment shown in FIG. 3 is the ejection mechanism with repetition stop provided therein, the main parts of which are a ratchet lever 86 and an abutment 87.

The function of the ejection mechanism with the repetition stop is more clearly shown in FIGS. 4a, 4b, 5 and 6. The ratchet lever 86 is tiltable about an axis 88 and has an operating arm 89 and a ratchet 90. It is incorporated into the lancet holder 52 in the manner shown in these Figures.

FIGS. 4a, b show a lancet holder with an inserted lancet 91. The lancet comprises, in the illustrated embodiment, a lancet tip 92 and a lancet body 93 of extruded synthetic resin. As can be seen more clearly from FIGS. 4a and 6, the lancet body has recesses 94 behind which the ratchet of the ratchet lever 86 engages in order to hold the lancet 91. From FIG. 6, there can be seen in cross-section that the lancet has a symmetrical cross-section with four recesses so that it can be inserted by the user of the device into practically any position of the lancet holder 52. For guiding and orienting the lancet, the lancet holder 52 has oblique run-in surfaces 95.

In the Figures, there can also be seen a U-shaped weight 96 which is movable in a vertical direction in appropriate guides and lies against the upper edge of the lancet 91. Finally, there can also be seen a spring 99 which biases the ratchet lever 86 in a clockwise direction, i.e. in the closing direction of the ratchet.

In the following, there is described, with reference to FIGS. 4 to 6, the ejection and tensioning operation of the lancet and the introduction of a new lancet. This procedure follows, in each case, the previously described puncturing operation, it being important that the stroke of the lancet holder in the case of the puncturing operation is so small that the arm 89 of the ratchet lever 86 does not come into contact with the abutment 87.

For the ejection, the lancet is moved downwardly via the operating knob 59 of the lancet holder until it is in the position illustrated in FIG. 4a. By means of the abutment 87, the operating arm 89, upon further downward pressing, is moved outwardly to the right, the ratchet 90 thereby also moving to the right and freeing the lancet body. The weight 96, together with the lancet holder, receives a downward impulse by operation of the knob 59. When this downwards direction is then interrupted by impingement of the operating arm 89 on the abutment 87, the weight exerts, because of its inertia since it is movably mounted in a vertical direction, an impulse upon the lancet holder. In this way, even comparatively lightly constructed lancets, which are correspondingly cheap to produce, can be dependably ejected.

When the lancet 91 has been ejected, the ratchet lever 86, driven by the spring 99, moves clockwise and the operating arm 89 comes into a position which no longer lies in the range of action of the abutment 87 (see FIG. 4b).

For the reception of a new lancet, the lancet holder can now be moved further downwardly. A new lancet is now inserted from below by the user, through opening 79, the lancet holder thereby being in a position which is lower than that illustrated in FIG. 4b.

Upon insertion of the lancet 91, the ratchet lever 86 is turned back against the spring force and the ratchet 90 engages behind the corresponding recess 94 of the lancet body 93. The operating arm 89 of the ratchet lever 96 is thereby moved to the right in such a manner that member 100 is present in the region of the abutment 87.

The ratchet lever 86 is, especially in the region of its operating arm 89, made of elastic material so that it is possible, upon releasing the operating knob 59, for the lancet holder 52 to be forced back upwardly by the spring 6, the right outer side of the ratchet lever 86 thereby impinging against the abutment 87.

After the lancet holder 52 has thus returned to its resting position, the position illustrated in FIG. 3 is again achieved in which a new puncturing operation can be initiated.

What is claimed is:

1. A blood lancet device comprising: a housing having a lancet exit opening; means receptive of a lancet for guiding same in the housing for movement between a retracted position and a puncturing position wherein the lancet projects from the exit opening; means for releasably spring loading the lancet into the retracted position for impulse-like movement into the puncturing position upon release with immediate return movement towards the retracted position, the releasable spring loading means comprising a movable stop membber for retaining the lancet in the retracted position, two springs, the first spring for applying a force to move the lancet towards the puncturing position and the second spring for applying a force to immediately thereafter move the lancet towards the retracted position and means for transmitting the force of the first spring to the lancet and for discontinuing the application of the force by the first spring during the movement of the lancet towards the puncturing position; and triggering means for moving the stop member to enable movement from the retracted position to the puncturing position.

2. The device according to claim 1, wherein when the second spring allies its force simultaneously with and opposite to the force of the first spring during movement from the retracted to the puncturing position, the force of the second spring is less than that of the first spring in the range of movement of the lancet in which the force of the first spring is applied.

3. The device according to claim 1 or 2, wherein the guiding means includes a lancet holder with a striker surface thereon and the force transmitting means includes an angled lever pivotable about an axis fixed to the housing and comprising a rigidly connected striker engageable with the striker surface on the lancet holder, an extension arm to which the first spring is connected, and the means for discontinuing the application of force by the first spring includes a recess in the lancet holder for receiving the striker to discontinue the connection between the striker and the lancet.

4. The device according to claim 1, wherein the triggering means comprises a movable release member surrounding the lancet exit opening which is positioned to be not visible to the subject as the device approaches the surface of the part of the body from which blood is to be obtained.

5. The device according to claim 4, wherein the trigger means comprises a pusher acting on the movable stop member and connected to the release member and means spring biasing the release member outwardly of the exit opening.

6. The device according to claim 4, wherein the release member comprises a removable trigger cap which projects from the housing and the thickness of which determines the depth of penetration of the lancet.

7. The device according to claim 4, wherein the second spring comprises a compression spring supported on both the lancet and the housing.

8. The device according to claim 4, wherein the guiding means comprises a lancet holder and means for releasably retaining a lancet in the lancet holder.

9. The device according to claim 8, wherein the means for releasably retaining the lancet includes a movable pushbutton projecting from the housing to release a lancet and to move the holder into a position to accept a lancet.

10. The device according to claim 9, wherein the releasable retaining means includes a latching lever pivotably mounted to the holder around a second axis and having a catch engageable with a recess in the lancet to hold it in place and an activating arm on the end facing away from the catch and a support on the housing for actuating the arm to move the catch out of the recess when the movable pushbutton moves the holder into the position for accepting a lancet.

11. The device according to claim 10, wherein the second axis for the latching lever, the catch and the position at which the support engages the activating arm are such that the support will exert a force on the latching lever in the direction in which the catch closes when the holder retracts.

12. The device according to claim 11, wherein the latching lever is essentially U-shaped with open portion facing the exit opening, both the point at which the support engages the activating arm and the catch are positioned along each arm of the U toward its ends and the second axis is positioned nearer its midpoint.

13. The device according to claim 8, wherein the holder further comprises a weight that is positioned therein above the lancet and which is movable in relation to the holder to contact the lancet when it has been inserted.

* * * * *